United States Patent [19]
Evenstad et al.

[11] Patent Number: 5,126,145
[45] Date of Patent: Jun. 30, 1992

[54] CONTROLLED RELEASE TABLET CONTAINING WATER SOLUBLE MEDICAMENT

[76] Inventors: Kenneth L. Evenstad, 16235 Holdridge Rd., Wayzata, Minn. 55391; Kuldip R. Malhotra, 2558 Ridge La., Moundsview, Minn. 55112; Victoria A. O'Neill, 830 Kingsview La., Plymouth, Minn. 55447

[21] Appl. No.: 536,184

[22] Filed: Jun. 11, 1990

Related U.S. Application Data

[63] Continuation of Ser. No. 337,460, Apr. 13, 1989, abandoned.

[51] Int. Cl.$^5$ ............ A61K 9/20; A61K 9/22
[52] U.S. Cl. .................... 424/465; 424/468; 424/469; 424/470; 424/488; 424/499; 424/502; 514/960; 514/964
[58] Field of Search ........ 424/488, 469, 470, 465, 424/489

[56] References Cited

U.S. PATENT DOCUMENTS

| | | | |
|---|---|---|---|
| 3,870,790 | 3/1975 | Lowey et al. | 424/19 |
| 4,259,314 | 3/1981 | Lowey | 424/19 |
| 4,369,172 | 1/1983 | Schor et al. | 424/19 |
| 4,389,393 | 6/1983 | Schor et al. | 424/19 |
| 4,680,323 | 7/1987 | Lowey | 524/43 |
| 4,756,911 | 7/1988 | Drost et al. | 424/470 |

FOREIGN PATENT DOCUMENTS 0109320  6/1986  France.

OTHER PUBLICATIONS

Methocel as a Binding Agent for Tablet Production by Wet Granulation, Dow Chemical U.S.A., 1985.
Formulating for Controlled Release with Methocel Cellulose Ethers, Dow Chemical U.S.A., 1987.

Primary Examiner—Thurman K. Page
Assistant Examiner—James M. Spear

[57] ABSTRACT

A sustained or controlled release tablet is disclosed. The tablet comprises a water soluble medicament, a hydroxypropyl methylcellulose having sustaining action, a pharmaceutical binding agent, and a hydrophobic component.

24 Claims, 2 Drawing Sheets

CONTROLLED RELEASE TABLET CONTAINING WATER SOLUBLE MEDICAMENT

This is a continuation of application Ser. No. 07/337,460, filed Apr. 13, 1989 now abandoned.

This, invention relates to a controlled release tablet comprising hydroxypropyl methylcellulose, a binding agent, an internal hydrophobic component, and water soluble medicament. The tablet can be formed by wet granulation techniques.

BACKGROUND OF THE INVENTION

Sustained or controlled release products for oral administration are known and widely used. Hydroxypropyl methylcellulose has been used in such products. It is believed that hydroxypropyl methylcellulose in such tablets partially hydrates on the tablet surface to form a gel layer. The rate of hydration and gelling of the hydroxypropyl methylcellulose tablet surface affects the drug release from the tablet and contributes significantly to the sustained release aspect of such products.

However, it has been difficult to formulate controlled release tablets of soluble medicaments and hydroxypropyl methylcellulose. First, it has been difficult to achieve the desired dissolution profiles or to control the rate of release of soluble to freely soluble medicaments. This may be due to leaching of the medicament from the tablet before hydration and gelling of the hydroxypropyl methylcellulose occurs. Second, known tableting techniques such as direct compression and granulation may fail when a high proportion of soluble medicament is required regardless of its degree of solubility.

Bead coating technology can be used to form sustained release products. These products typically comprise hard gelatin capsules containing coated beads of medicament. Soluble medicaments are available in controlled release capsules of this type. However, tablets have certain advantages over capsules and these advantages are lost with the use of capsules for sustained release of soluble therapeutic agents.

Tablets have several advantages over capsules. For some drugs, it is recommended that the patient begin taking a smaller dose and gradually over time increase the dose to the desired level. This can help avoid undesirable side effects. Tablets can be preferable to capsules in this regard because a scored tablet easily can be broken to form a smaller dose.

In addition, tableting processes such as wet granulation are generally simpler and less expensive than bead coating and capsule formation. Further, tablets can be safer to use because they may be less subject to tampering.

Accordingly, a need exists for a controlled release product of more soluble medicaments, combining the advantages of hydroxypropyl methylcellulose in sustaining and controlling the release rate, the relative ease and low cost of wet granulation, and the other advantages of the tablet form over capsules.

BRIEF DESCRIPTION OF THE INVENTION

We have discovered a sustained release tablet comprising hydroxypropyl methylcellulose with sustaining properties but negligible binding properties, in an amount effective to produce a desired release rate, sufficient water soluble pharmaceutical binder to permit wet granulation, an amount of internal hydrophobic component effective to permit wet granulation, and a water soluble medicament.

DETAILED DESCRIPTION OF THE E INVENTION

Figure 1:
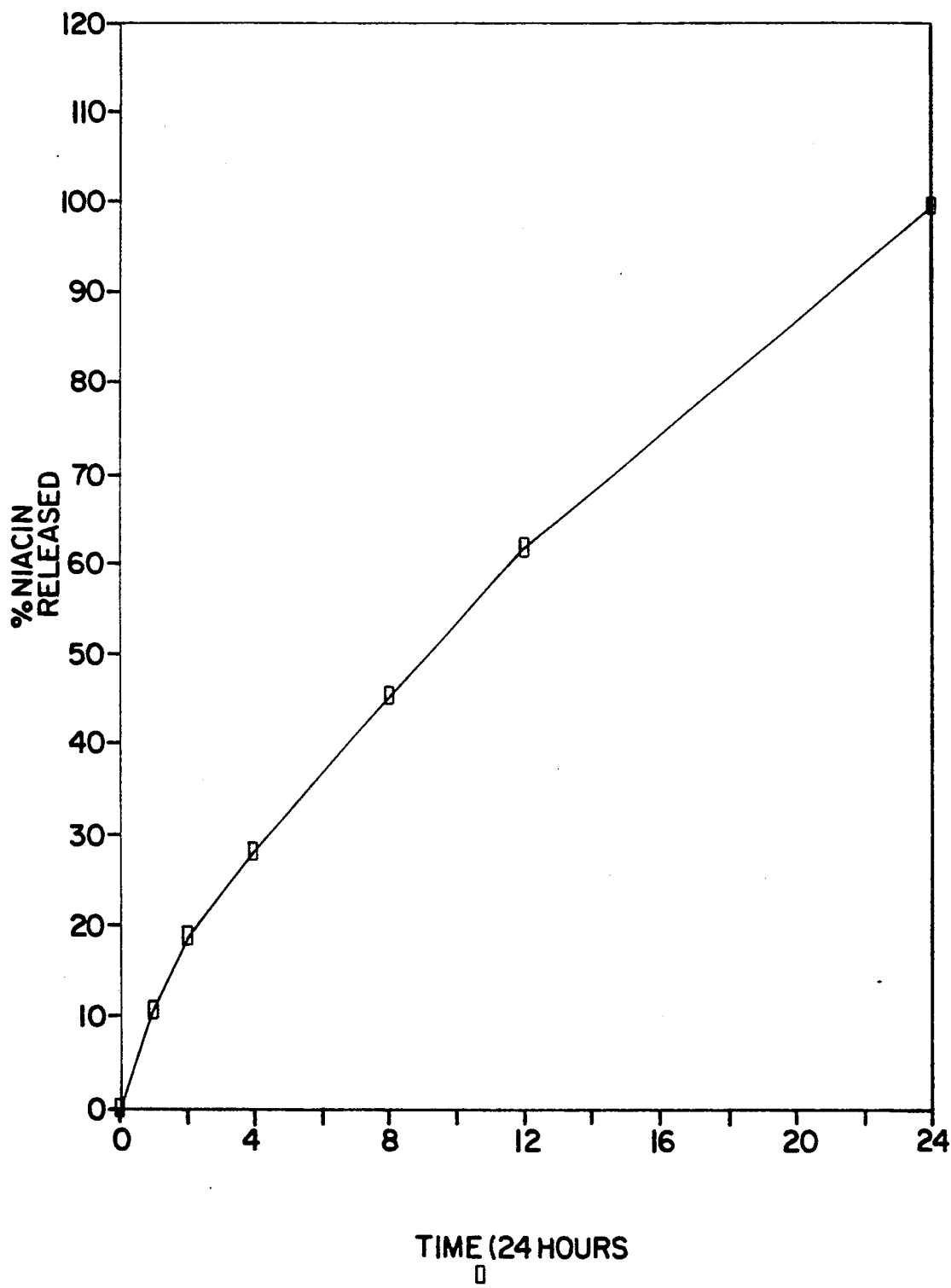
FIG. 1 is a graph showing an average dissolution profile of 750 mg. niacin tablets made in accordance with the invention.
Figure 2:
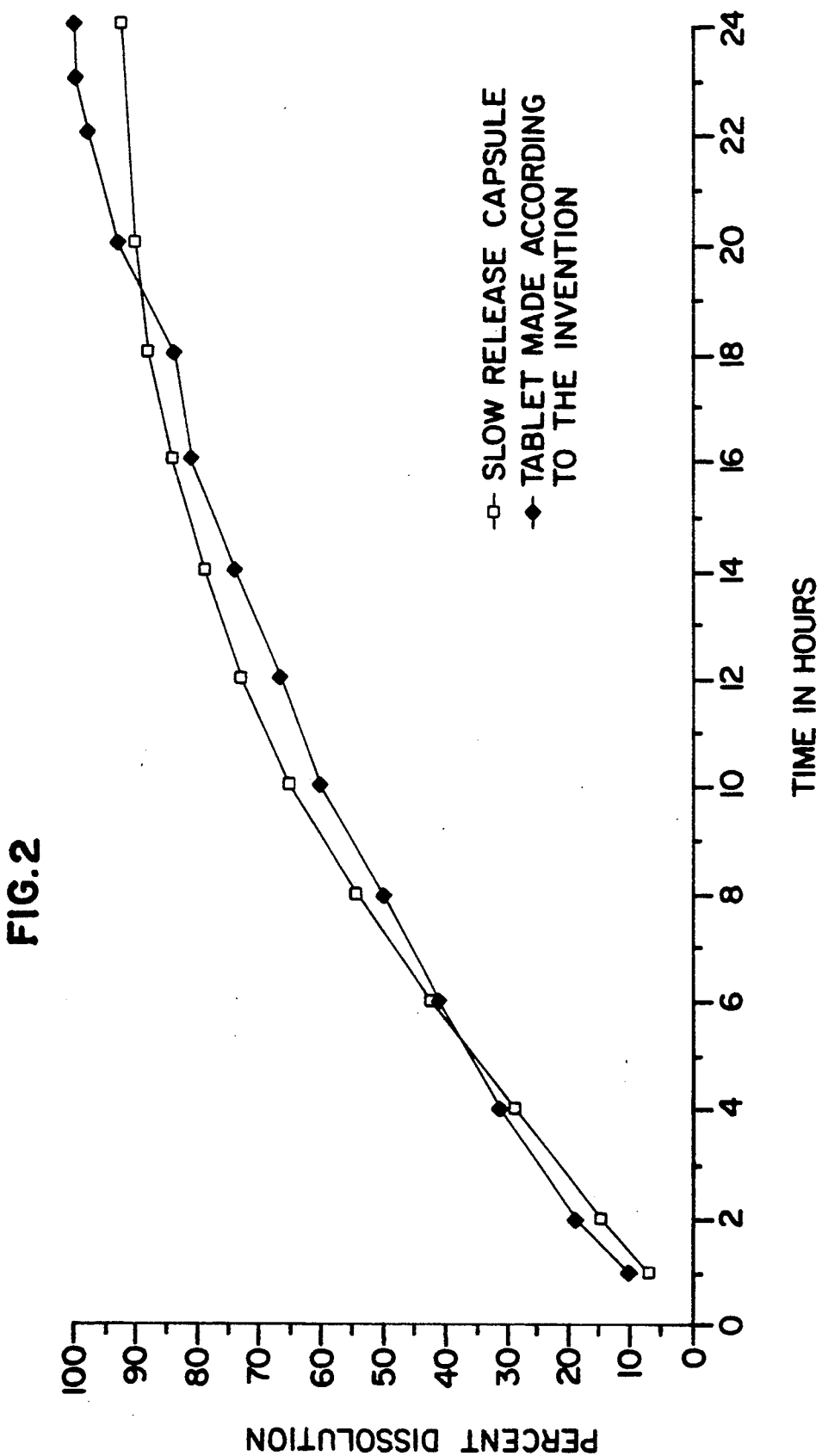
FIG. 2 is a graph comparing the average dissolution profiles of niacin (500 mg) tablets made in accordance with the invention and a commercially available extended-release niacin (500 mg) capsule.

The controlled release tablet includes a medicament and a hydrophillic polymer matrix for achieving controlled or sustained or extended release of the medicament. The tablet can include a high proportion of water soluble medicament and can be prepared by standard wet granulation techniques. A desirable dissolution profile can be achieved. The tablet can be scored to permit easy titration up to the desired dose.

The medicament can be any suitable water soluble therapeutically active material which is commonly administered orally. The medicaments that we believe will benefit most from the invention are those that appear to be too soluble for ready inclusion in an effective controlled release tablet utilizing hydroxypropyl methylcellulose. The solubility of the medicaments could from about 0.1 to 30% (at 25° C.). This includes slightly soluble to freely soluble compounds, according to the definitions provided by Remington Pharmaceutical Sciences.

The minimum amount of medicament or active drug in the tablets of the invention will typically be about 30% by weight based on the weight of the tablet and can range up to about 90%. Within this range, generally it is possible to incorporate a greater amount of a less soluble medicament.

Niacin, with a water solubility of about 1.67 g/100ml (25° C.), is a medicament falling within the scope of the invention. Niacin has the chemical formula $C_6H_5NO_2$ and is also known as nicotinic acid. It is commercially available as fine white crystals or white crystalline powder, from sources such as Lonza and Ashland Chemical. It will typically be present at a level of from 50–85% by weight of the tablet. Other therapeutically active materials suitable for use in the invention include morphine sulfate, chlorpheniramine hydrochloride, pseudoephedrine, codeine sulfate and diltiazem hydrochloride, aspirin, acetaminophen, and naproxen.

The hydrophillic polymer matrix of the tablets of the invention is a dynamic system involving hydroxypropyl methylcellulose wetting, hydration, and dissolution. Other soluble excipients or drugs also wet, dissolve, and diffuse out of the matrix while insoluble materials are held in place until the surrounding polymer/excipient/drug complex erodes or dissolves away.

The most significant mechanism by which drug release is controlled is through the use of hydroxypropyl methylcellulose. The hydroxypropyl methylcellulose, present throughout the tablet, partially hydrates on the tablet surface to form a gel layer. Overall dissolution rate and drug availability are dependent on the rate of soluble drug diffusion through the wet gel and the rate of tablet erosion. Hydroxypropyl methylcellulose with substitution rates of about 7–30% for the methoxyl group and greater than 7% or about 7–20% for the hydroxypropoxyl group are preferred for formation of this gel layer. More preferred are substitution rates of 19-30% for the methoxyl group and 7-12% for the hydroxypropyl group.

Hydroxypropyl methylcelluloses vary in their viscosity, methoxy content, and hydroxypropoxyl content. Properties also vary. Some have more sustaining properties or the ability to achieve conrolled release of medicaments. Others have good binding properties and are less desirable for sustained properties. By "binding properties" we are referring to the ability to act as a binding agent for tablet production by wet granulation, for example, incorporating the hydroxypropyl methylcellulose into aqueous solution in order to spray onto the dry powders. Hydroxypropyl methylcelluloses with good sustaining properties are too viscous for use as the binder in wet granulation techniques.

The tablets of the invention comprise about 5-30 percent by weight hydroxypropyl methylcellulose with sustaining properties and negligible binding properties. Such hydroxypropyl methylcelluloses generally have a viscosity of no less than about 1000 centipoises.

More typically, the viscosity will be no less than about 4000 cps. For improved performance, the tablet will comprise about 5-20 weight percent, or, more preferably, about 8-12 percent hydroxypropyl methylcellulose with sustaining characteristics.

A preferred hydroxypropyl methylcellulose with sustaining properties is a hydroxypropyl methylcellulose with substitution type 2208, with a nominal viscosity, 2% aqueous, of about 100,000 cps, a methoxyl content of about 19-24%, and a hydroxypropoxyl content of about 7-12%. A "controlled release" grade is preferred, with a particle size where at least 90% passes through a #100 USS mesh screen. A commercially-available hydroxypropyl methylcellulose meeting these specifications is the Methocel K100MCR, from The Dow Chemical Company.

The tablet further comprises or includes about 2-15 weight percent water soluble pharmaceutical binder. The binder or binding agent aids in tablet production by wet granulation, serving as an adhesive and adding strength to the tablet.

Many suitable binders are known. They include polyvinyl pyrollidone, starch, gelatin, sucrose, lactose, methylcellulose, hydroxypropyl methylcellulose, and the like. For good binding action without excess binding agent, we prefer the use of about 2-8% by weight, or more preferably, particularly where the preferred binding agent is used, about 2-5% by weight.

The preferred water soluble pharmaceutical binder for use in this invention is hydroxypropyl methylcellulose having binding properties. Such hydroxypropyl methylcelluloses typically have a much lower viscosity than the hydroxypropyl methylcelluloses that have good sustaining characteristics. Generally, the viscosity of a 2% aqueous solution will be less than about 1000 cps. More typically, it will be less than 100 cps.

A preferred hydroxypropyl methylcellulose for use as a binding agent in the context of the invention has a nominal viscosity, 2% aqueous, of about 15, a methoxy content of about 28-30%, a hydroxypropyl content of about 7-12%, and a particle size of 100% through USS 30 mesh screen and 99% through USS 40 mesh screen. Hydroxypropyl methylcellulose 2910, Methocel E15 from The Dow Chemical Company meets these standards and is a preferred binder.

Other suitable binding hydroxypropyl methylcelluloses include Methocel E5LVP, Methocel E50LVP, and Methocel K3P. The methylcellulose Methocel AI5LVP can also be used.

Another binder we recommend is polyvinyl pyrollidone, also known as polyvidone, povidone, and PVP. Typical properties of commercially available PVP's include density between 1.17 and 1.18 g/ml and an average molecular weight ranging from about 10,000 to 360,000. Generally, the higher molecular weight PVP's would be more suitable for use in this invention. Suppliers include BASF Wyandotte and GAF.

An essential component of the invention is what we refer to as the hydrophobic component. This component permits wet granulation of soluble medicaments with hydroxypropyl methylcellulose where it would not otherwise be easily accomplished using standard wet granulation techniques. In the absence of this component, we have found that the hydroxypropyl methylcellulose/medicament mixture tends to become "doughy" and granules or powder cannot easily be obtained.

The hydrophobic component comprises a wax-like material. The wax-like material comprises a solid generally insoluble substance having a waxy consistency. It should, of course, be ingestible. Many such materials are known and include waxes such as beeswax, carnauba wax, candelilla wax, Japan wax, paraffin, hydrogenated castor oil, higher fatty acids, such as palmitic acid, stearic acid, and myristic acid, esters of such higher fatty acids such as substituted mono-, di-, and tri-glycerides, acetylated monoglycerides, glyceryl monostearate, glyceryl tristearate, cetyl palmitate, glycol stearate, glyceryl tri-myristate, higher fatty alcohols such as cetyl alcohol, stearyl alcohol, and myristyl alcohol, and mixtures thereof.

Two wax-like materials are preferred in view of their ready availability in powdered form, reasonable cost, ease of handling, and their effectiveness in the context of this invention. These waxy materials are hydrogenated vegetable oil and stearic acid. Hydrogenated vegetable oil generally consists mainly of the triglycerides of stearic and palmitic acids, and is readily commercially available. A preferred hydrogenated vegetable oil for use in this invention is available through Edward Mendell, Co., Inc., of N.Y., under the trademark Lubritab ®. The Lubritab ® product has a bulk density of 0.48-0.56 grams per milliliter, a melting point of from 61°-66° C., a saponification value of 188-198, 0.8 maximum unsaponifiable matter, and a typical particle size distribution of 15 percent maximum on 100 mesh USS screen, 35 percent maximum through 200 mesh USS screen. An advantage of this product is its availability in powder form. A similar hydrogenated vegetable oil is available from Durkee, under the trademark Duratex.

Stearic or octadecanoic acid is typically manufactured from fats and oils derived from edible sources, and commercial stearic acid is typically a mixture of stearic acid ($C_{18}H_{36}O_2$) and palmitic acid $C_{16}H_{32}O_2$). Stearic acid is available from many chemical suppliers, including Emery Industries and Mallinckrodt, Inc.

The powdered stearic acid NF available from Mallinckrodt contains not less than 40.0 percent $C_{18}H_{36}O_2$ and not less than 40.0 percent $C_{16}H_{32}O_2$; the sum of these two components is not less than 90.0 percent. The congealing temperature is not lower than 54°, and the iodine value is not more than 4.

The hydrophobic component should be present in an amount effective to permit wet granulation of the controlled release tablet. Such an amount is commonly 2-20 percent by weight of the tablet depending on the solubility of the medicament. Higher concentrations will be required for more soluble medicaments. Preferably, for good granulating results and sustained release, it will be present at from 5-15 percent of the total tablet weight, or more preferably, 6-12 percent by weight.

Other components commonly used in tablet formation, such as external lubricants, dyes, fillers and extenders, may also be used as desired. External lubricants or tableting aids can include calcium stearate, stearic acid, hydrogenated vegetable oils, talc, corn starch, colloidal silicone dioxide, magnesium stearate, and glyceryl behenate. We have found that a combination of glyceral behenate, magnesium stearate, and colloidal silicon dioxide is particularly effective as a tableting aid.

The external lubricants, typically added to the dried granules before tableting, if used, can be present at up to about 5 percent of the total tablet weight. More preferably, they will be present at 0.5-4 percent, or for improved tableting, 1-3 percent of the tablet weight.

Dyes can, of course, be used for a more pleasing tablet appearance. Many suitable ingestible dyes for tablets are known and are widely available.

Fillers or extenders can be used if needed or desired. When a tablet containing a 250, 500, or 750 mg. dose of niacin is formed, fillers or extenders typically would not be used because the medicament itself supplies sufficient volume to the tablet. However, fillers or extenders may be desirable where a lower dose of medicament is used. Many fillers or extenders are known and are readily available, including calcium sulfate, dicalcium phosphate, tricalcium phosphate, lactose, sucrose, starch dextrose, and microcrystalline cellulose.

The methods of forming the tablets of the invention are typical wet granulation methods, either conventional or fluid bed. A uniform blend of the hydrophobic component (flakes or powder) and dye, if used, is formed. The binding agent is dissolved in water to form a binding agent solution. The hydrophobic component blend, the sustaining hydroxypropyl methylcellulose, and the medicament are granulated using the binding agent solution to a final moisture level of less than about 7 percent, preferably less than about 5 percent. In the conventional process, the granulation is removed from the mixer and oven dried. External lubricating agents are then mixed in and the mixture is tableted. As would be understood by one of skill in the art, fluid bed processing would not require the oven drying step; instead the components would be granulated and dried in one procedure.

Where niacin is the medicament, useful tablets include doses of 250, 500, and 750 mg. High doses such as 750 mg. can cause side effects such as uncomfortable flushing and nausea unless treatment begins with smaller doses. Tablets can be scored to permit dasy breakage into smaller doses for titration up to the standard 750 mg. dose given twice daily. Titration, particularly with sustained release tablets, has been shown to help avoid side effects of niacin therapy.

Tablets made according to the invention can have desirable dissolution profiles mimicking zero order absorption characteristics or constant rate of release over time. Niacin tablets in accordance with the invention show dissolution profiles of 10-35% in 2 hours after ingestion, 40-70% in 8 hours, and at least 90% dissolution in 24 hours. Even more preferably, the profile of the niacin tablets is 10-30% release in 2 hours, 40-60% in 8 hours, and complete dissolution in 24 hours, and tablets in accordance with the invention have shown this profile.

The invention will be further understood by reference to the following Examples which include preferred embodiments.

EXAMPLE I 750 mg. niacin tablets were formed having the following components:

|  | % by Weight | Mg./Tablet |
| --- | --- | --- |
| Niacin (Lonza) | 73.07 | 750.0 |
| Hydroxypropyl Methylcellulose 2910 (Methocel E15LV, Dow) | 2.50 | 25.7 |
| Hydroxypropyl Methylcellulose 2208 (Methocel K100MCR, Dow) | 9.74 | 100.0 |
| Hydrogenated Vegetable Oil (Lubritab, Mendell) | 11.56 | 118.7 |
| Glyceryl Behenate (Compritol 888) | 0.50 | 5.1 |
| Magnesium Stearate (Mallinckrodt) | 1.50 | 15.4 |
| FD&C Red #40 Lake Dye (40%) (Colorcon) | 0.13 | 1.3 |
| Colloidal Silicon Dioxide (Syloid 244) | 1.00 | 10.3 |

To form the tablest, 16 liters of water was heated to 95° C. in a stainless steel container. The Methocel E15LV powder was slowly added while mixing until a homogenous suspension was obtained. The impeller speed was adjusted to avoid excessive air from entering the solution through the vortex.

48 liters of very cold water was slowly added and the mixture was mixed thoroughly until a clear solution was obtained and the temperature was below 20° C. Mixing continued for an additional 20 minutes.

The hydrogenated vegetable oil was sized through a USS No. 16 screen and added to a mixer. The dye was added to the mixer and mixed until the color distribution was uniform, about 5 minutes. The color mix was then transferred to a ribbon blender. The niacin powder was added to the ribbon blender and mixed for about 10 minutes. The Methocel K100MCR was then added and mixed for an additional 10 minutes.

The Methocel E15LV solution was sprayed in and then mixed for 1 minute. The resulting wet granulation was then sized through a USS No. 16 screen.

The sized wet granulation was spread lightly on trays, at approximately 2 kilograms per tray. The granulation was dried in an oven at 230° F. to a moisture content of less than 5 percent. The oven dried granulation was then sized through a USS No. 12 screen. After sizing, the granulation was collected in double poly-lined drums.

Three approximately 200 kilogram batches were formed in the above manner, each utilizing 149.06 kilograms niacin, 3.97 kilograms Methocel E15LV, 19.87 kilograms Methocel K100MCR, 24.84 kilograms Lubritab hydrogenated vegetable oil, and 0.26 kilograms FD&C Red Dye #40 Lake 40% pure dye. These batches were weighed, and combined in a ribbon blender. 3.0 kilograms glyceryl behenate and 3.0 kilograms magnesium stearate were then added to the ribbon blender and the mixture was mixed for 5 minutes.

The resulting product was tableted using a standard rotary press into tablets of 750 milligrams niacin.

EXAMPLE II 750 milligram niacin tablets were formed as follows:

| Per Part | Milligrams/ Tablet | Kilograms Used |
|---|---|---|
| Niacin (Lonza) | 750.00 | 312.500 |
| Hydroxypropyl Methylcellulose 2910 (Methocel E15LV, Dow) | 24.00 | 10.000 |
| Hydroxypropyl Methylcellulose 2208 (Methocel K100MCR, Dow) | 94.10 | 39.200 |
| Hydrogenated Vegetable Oil (Lubritab, Mendell) | 62.40 | 26.00 |
| FD&C Red #40 Lake Dye (40%) (Colorcon) | 0.70 | 0.300 |

The niacin tablets of Example II were formulated by the fluid bed process. Half of the above quantities were used for the first granulation. In this granulation, 33.000 kilograms deionized water were added to a stainless steel steam kettle and heated to 95° C. While mixing (but avoiding excess foaming), the Methocel E15LV and dye were added to the water. 67.000 kilograms cold deionized water were then added and mixing continued for about 20 minutes. The mixture was cooled to 21° C.

To the fluid bed container were added the niacin, Methocel K100MCR, and Lubritab hydrogenated vegetable oil. These three components were granulated with the Methocel E15LV solution. After exhausting the granulating solution, the material in the fluid bed containers was dried to less than 1% moisture.

The dried material was transferred to clean polylined containers. Using the Sweco Sifter, fitted with a 12 mesh screen, the granulation was sized into clean polylined drums.

A second batch of granulation was formed in an identical manner using the remaining half of the components. The two granulations were then added to a ribbon blender. These components were blended for 5 minutes. 6.000 kilograms magnesium stearate, 2.000 kilogram glyceral behenate, and 4.000 kilograms colloidal silicon dioxide were added to the ribbon blender and mixed for 5 minutes. The material was transferred to clean poly-lined drums and later tableted into tablets containing 750.00 milligrams niacin.

Two other formulations are shown below.

EXAMPLE III

| Chemical Name | Milligrams/Tab | Percent |
|---|---|---|
| Niacin | 750.0 | 78.125 |
| Methocel E15LV (hydroxypropyl methylcellulose) | 24.0 | 2.50 |
| Methocel K100MCR (hydroxypropyl methylcellulose) | 94.1 | 9.80 |
| Lubritab (hydrogenated vegetable oil) | 62.4 | 6.50 |
| FD&C Red #40 dye | 0.7 | 0.075 |
| Magnesium Stearate | 14.4 | 1.50 |
| Compritol (glyceryl behenate) | 4.8 | 0.50 |
| Syloid 244 (colloidal silicon dioxide) | 9.6 | 1.00 |

Tablets having the formulation of example III were made using conventional and fluid bed granulating techniques in a production mode.

FIG. 1 shows the average dissolution pattern of six tablets having the formula shown in Example III.

Tablest were dissolved using a Hanson Dissolution Apparatus with a U.S.P. rotating bracket at 100 rpm in 900 ml. water at 37° C. Samples were taken from each dissolution vessel at 1, 2, 4, 8, 12, and 24 hours, and analyzed by UV for nicotinic acid content. The results show a desirable release pattern.

| Chemical Name | Milligrams/Tab | Percent |
|---|---|---|
| Niacin | 750.0 | 76.220 |
| Methocel E15LV (hydroxypropyl methylcellulose) | 24.0 | 2.439 |
| Methocel K100MCR (hydroxypropyl methylcellulose) | 94.1 | 9.561 |
| Lubritab (hydrogenated vegetable oil) | 86.4 | 8.780 |
| FD&C Red #40 dye | 0.7 | 0.073 |
| Magnesium Stearate | 14.4 | 1.463 |
| Compritol (glyceryl behenate) | 4.8 | 0.488 |
| Syloid 244 (colloidal silicon dioxide) | 9.6 | 0.976 |

Tablets having the formulation of Example IV were made using conventional granulating techniques in the laboratory.

| Chemical Name | By Weight % | Mg./Tablet |
|---|---|---|
| Niacin | 73.07 | 500.00 |
| Methocel E15LV (hydroxypropyl methylcellulose) | 2.50 | 17.11 |
| Methocel K100MCR (hydroxypropyl methylcellulose) | 9.74 | 66.65 |
| Lubritab (hydrogenated vegetable oil) | 11.56 | 79.10 |
| Compritol 888 (glyceryl behenate) | 0.50 | 3.42 |
| Magnesium Stearate | 1.50 | 10.26 |
| FD&C Red #40 dye | 0.13 | .89 |
| Syloid 244 (colloidal silicon dioxide) | 1.00 | 6.84 |

Tablets having the composition shown in Example V were made using conventional and fluid bed techniques. The dissolution pattern of tablets made in accordance with the formula of Example V was compared with the dissolution pattern of a typical commercially available extended release capsule, 500 mg. niacin. Six samples of each product were dissolved using a Hanson Dissolution Apparatus with a U.S.P. rotating basket at 100 rpm in 900 ml. of water at 37° C. Samples were taken from each dissolution vessel over a 24-hour period, and analyzed by UV for nicotinic acid content. As shown in FIG. 3, the tablets of the invention followed by similar profile to the commercially available extended release capsules, 500 mg. niacin.

| Chemical Name | By Weight % Total | Mg/Tablet |
|---|---|---|
| Niacin | 73.07 | 250.00 |
| Methocel E15LV (hydroxypropyl methylcellulose) | 2.50 | 8.55 |
| Methocel K100MCR (hydroxypropyl methylcellulose) | 9.74 | 33.32 |
| Lubritab (hydrogenated vegetable oil) | 11.56 | 39.55 |
| Compritol 888 | 0.50 | 1.71 |

| Chemical Name | By Weight % Total | Mg/Tablet |
| --- | --- | --- |
| (glyceryl behenate) | | |
| Magnesium Stearate | 1.50 | 5.13 |
| FD&C Red #40 dye | 0.13 | .45 |
| Syloid 244 (colloidal silicon dioxide) | 1.00 | 3.42 |

Tablets having the composition shown in Example VI were made using conventional and fluid bed techniques.

The foregoing description and examples are illustrative of the invention. However, since persons skilled in the art can make various embodiments without departing from the spirit and scope of the invention, the invention is embodied in the claims hereafter appended.

We claim:

1. A controlled release uncoated tablet comprising:
   (a) about 5-20 percent by weight hydroxypropyl methylcellulose having a viscosity of about 1000 or greater, a substitution rate for the methoxyl group of about 7-30% and a substitution rate for the hydroxypropoxyl group of about 7-20%;
   (b) about 2-8 percent by weight hydroxypropyl methylcellulose having a viscosity of less than about 1000, methyl cellulose, or polyvinyl pyrollidone;
   (c) about 5-15 percent by weight hydrogenated vegetable oil or stearic acid; and
   (d) a therapeutically active material having a water solubility of about 0.1-30% at normal room temperature;
   wherein said tablet has a dissolution profile, with a substantially zero order absorption characteristic, of about 10-35% within 2 hours after ingestion.

2. A controlled release uncoated tablet comprising:
   (a) about 5-30 percent by weight hydroxypropyl methylcellulose with sustaining properties;
   (b) about 2-15 percent by weight water soluble pharmaceutical binder;
   (c) about 2-20 percent by weight hydrophobic component; and
   (d) a medicament having a solubility of about 0.1 to 30 wt-% in water;
   wherein said tablet has a dissolution profile, with a substantially zero order absorption characteristic, of about 10-35% within 2 hours after ingestion.

3. The controlled release tablet of claim 2 wherein the water soluble medicament comprises niacin and forms about 50-85 percent by weight of the tablet.

4. The controlled release tablet of claim 2 wherein the hydroxypropyl methylcellulose comprises a hydroxypropyl methylcellulose having a nominal viscosity, 2 percent aqueous solution, of about 100,000 cps, a methoxyl content of about 19-24 percent, a hydroxypropoxyl content of about 7-12 percent, and a particle size where at least 90 percent passes through a USS 100 mesh screen.

5. The controlled release tablet of claim 2 wherein the water soluble pharmaceutical binder is selected from the group consisting of hydroxypropyl methylcellulose having binding properties, polyvinyl pyrollidone, methyl cellulose, gelatin, starch, sucrose, and lactose.

6. The controlled release tablet of claim 5 wherein the water soluble pharmaceutical binder comprises hydroxypropyl methylcellulose having binding properties.

7. The controlled release tablet of claim 5 wherein the water soluble pharmaceutical binder comprises polyvinyl pyrollidone.

8. The controlled release tablet of claim 6 wherein the hydroxypropyl methylcellulose having binding properties comprises hydroxypropyl methylcellulose having a nominal viscosity, 2 percent aqueous solution, of about 15 cps, a methoxy content of about 28-30 percent, a hydroxypropoxyl content of about 7-12 percent, and a particle size of 100% through a USS No. 30 mesh screen and 99% through a USS No. 40 mesh screen.

9. The controlled release tablet of claim 2 wherein the hydrophobic component comprises a wax-like insoluble material.

10. The controlled release tablet of claim 9 wherein the wax-like insoluble material is selected from the group consisting of hydrogenated vegetable oil and stearic acid.

11. The controlled release tablet of claim 10 wherein the wax-like insoluble material comprises a hydrogenated vegetable oil, the hydrogenated vegetable oil comprising a triglyceride of stearic acid.

12. The controlled release tablet of claim 2 further comprising up to about 5 percent by weight external lubricant.

13. The controlled release tablet of claim 12 wherein the external lubricant comprising glyceryl behenate.

14. The controlled release tablet of claim 13 wherein the external lubricant further comprises magnesium stearate.

15. The controlled release tablet of claim 2 wherein the hydroxypropyl methylcellulose with sustaining properties forms about 5-20 percent by weight of the tablet, the water soluble pharmaceutical binder forms about 2-8 percent by weight of the tablet, and the hydrophobic component forms about 5-15 percent by weight of the tablet.

16. The controlled release tablet of claim 3 wherein the percentage of niacin released in the 2 hours following following ingestion of the tablet is about 10-30 percent by weight.

17. The controlled release tablet of claim 3 wherein the percentage of the niacin released in the 8 hours following ingestion of the tablet is about 40-70 percent by weight.

18. The controlled release tablet of claim 17 wherein at least 90% release of the niacin occurs within 24 hours following ingestion of the tablet.

19. The controlled release tablet of claim 2 wherein the tablet is readily divisible into portions, each portion forming a smaller dose than the dose of the intact tablet.

20. The controlled release tablet of claim 3 wherein the tablet contains about 250 milligrams of niacin.

21. The controlled release tablet of claim 3 wherein the tablet contains about 500 milligrams of niacin.

22. The controlled release tablet of claim 3 wherein the tablet contains about 750 milligrams of niacin.

23. The controlled release tablet of claim 1 wherein the therapeutically active material forms from about 30-90% by weight of the tablet.

24. The controlled release tablet of claim 1 wherein the therapeutically active compound comprises niacin and forms from about 50-85 percent by weight of the tablet.

* * * * *

UNITED STATES PATENT AND TRADEMARK OFFICE
CERTIFICATE OF CORRECTION

PATENT NO. : 5,126,145

DATED : June 30, 1992

INVENTOR(S) : KENNETH L. EVENSTAD et al.

It is certified that error appears in the above-identified patent and that said Letters Patent is hereby corrected as shown below:

On the title page:   please insert:

--[73] Assignee: Upsher-Smith Laboratories, Inc., Minneapolis, Minnesota--

In col. 10, ln. 43, please delete the word "following" after the word "following" and before the word "ingestion".

Signed and Sealed this

Fourteenth Day of September, 1993

*Attest:*

BRUCE LEHMAN

*Attesting Officer*   *Commissioner of Patents and Trademarks*